(12) United States Patent
Yamamoto et al.

(10) Patent No.: US 8,765,176 B2
(45) Date of Patent: Jul. 1, 2014

(54) METHOD OF MANUFACTURING TABLET

(75) Inventors: Keiichi Yamamoto, Nishinomiya (JP);
Yoshio Mizukami, Amagasaki (JP);
Daisuke Izutsu, Dublin (IE)

(73) Assignee: Takeda Pharmaceutical Campany Limited, Osaka (JP)

( * ) Notice: Subject to any disclaimer, the term of this patent is extended or adjusted under 35 U.S.C. 154(b) by 84 days.

(21) Appl. No.: 10/477,478

(22) PCT Filed: Jun. 19, 2002

(86) PCT No.: PCT/JP02/06087
§ 371 (c)(1),
(2), (4) Date: Nov. 12, 2003

(87) PCT Pub. No.: WO03/000169
PCT Pub. Date: Jan. 3, 2003

(65) Prior Publication Data
US 2004/0131675 A1    Jul. 8, 2004

(30) Foreign Application Priority Data

Jun. 20, 2001  (JP) .................................. 2001-186433

(51) Int. Cl.
| | | |
|---|---|---|
| *A61K 9/20* | (2006.01) | |
| *A61K 9/28* | (2006.01) | |
| *B29C 41/32* | (2006.01) | |
| *B29C 41/46* | (2006.01) | |
| *B30B 15/34* | (2006.01) | |
| *A61J 3/10* | (2006.01) | |
| *A61J 3/00* | (2006.01) | |
| *A61K 9/24* | (2006.01) | |
| *A61K 9/00* | (2006.01) | |
| *B30B 11/08* | (2006.01) | |
| *A61K 9/50* | (2006.01) | |

(52) U.S. Cl.
CPC ............. *A61K 9/2095* (2013.01); *A61K 9/5078* (2013.01); *B30B 15/34* (2013.01); *A61J 3/10* (2013.01); *A61K 9/5026* (2013.01); *A61J 3/007* (2013.01); *A61K 9/209* (2013.01); *A61K 9/2081* (2013.01); *A61K 9/0056* (2013.01); *B30B 11/08* (2013.01)
USPC ............................... 424/465; 424/474; 264/77

(58) Field of Classification Search
USPC .......................................................... 424/465
See application file for complete search history.

(56) References Cited

U.S. PATENT DOCUMENTS

| | | | | |
|---|---|---|---|---|
| 4,230,693 | A | | 10/1980 | Izzo et al. ...................... 424/156 |
| 4,601,866 | A | | 7/1986 | David et al. .................... 264/109 |
| 4,713,248 | A | * | 12/1987 | Kjornaes et al. ............... 424/468 |
| 6,174,902 | B1 | * | 1/2001 | Yelle et al. ..................... 514/338 |
| 6,248,355 | B1 | * | 6/2001 | Seth ............................... 424/458 |
| 2002/0042433 | A1 | * | 4/2002 | Yelle et al. ..................... 514/338 |

FOREIGN PATENT DOCUMENTS

| | | |
|---|---|---|
| CA | 2 361 303 | 11/2007 |
| EP | 0 711 828 | 5/1996 |
| JP | 25-884 B | 3/1950 |
| JP | Y 7-39515 | 9/1995 |
| JP | A-9-47900 | 2/1997 |
| JP | B-2821089 | 8/1998 |
| JP | A-2000-103731 | 4/2000 |
| JP | 2001-26533 | 1/2001 |
| JP | A-2000-281564 | 10/2001 |
| WO | WO 9402140 A1 * | 2/1994 |
| WO | WO 96/01624 | 1/1996 |
| WO | WO 9712580 A3 * | 6/1997 |
| WO | WO 9959544 A2 * | 11/1999 |

OTHER PUBLICATIONS

Ketolainen et al., Temperature changes during tabletting measured using infrared thermoviewer, International Journal of Pharmaceutics, vol. 92, Issue 1-3, 1993, pp. 157-166 (abstract).*
Kikusui Seisakusho LTD. What is Rotary press? Tableting tchnology, tableting process and tableting process flow.*

* cited by examiner

*Primary Examiner* — Michael G Hartley
*Assistant Examiner* — Nabila Ebrahim
(74) *Attorney, Agent, or Firm* — Hamre, Schumann, Mueller & Larson, P.C.

(57) ABSTRACT

A method of manufacturing a tablet containing coated granules comprising compressing the coated granules containing biologically active substance and having a temperature exceeding a room temperature, whereby the tablet can be prevented from rupture of a part of a coating film of the granules at the time of tablet compression.

37 Claims, 3 Drawing Sheets

METHOD OF MANUFACTURING TABLET

TECHNICAL FIELD

The present invention relates to a method of manufacturing a tablet.

BACKGROUND ART

With increase in an aging population and change in the life environment, it is desired to develop an oral disintegrating-type solid preparation which can be easily taken, and can be handily and arbitrarily taken at any time anywhere without water, while maintaining convenient handling characteristics of tablets.

On the other hand, when a physiologically active substance is a substance exhibiting bitterness, from a viewpoint of drug taking observance, desirably, bitterness is masked by coating this substance. In addition, when a physiologically active substance is a substance liable to be degraded with an acid, it is necessary to coat the substance to prevent degradation by gastric acid and sufficiently deliver the substance to intestines. For these subjects, usually, coating tablets and capsules are used.

Although both are inconsistent requirements, as preparations which satisfy these requirements simultaneously, tablets comprising coated fine particles have been developed heretofore in the prior art. For example, JP 6-502194 A (U.S. Pat. No. 5,464,632) discloses a rapidly disintegrating multi-particle tablet characterized in that an effective substance is present in the form of coated fine particles and the like. Further, JP 2000-281564 A discloses an oral disintegrating tablet comprising coated fine particles in the tablet.

However, in the manufacture of a tablet comprising coated granules, there is a problem that, sometimes, a part of a coating film of the granules is ruptured during table compression, and there are problems that this decreases the aforementioned effect of masking bitterness, and reduces the acid resistance.

OBJECTS OF THE INVENTION

Therefore, an object of the present invention is to prevent rupture of a part of a coating film of coated granules at the time of tablet compression in the manufacture of a tablet comprising the coated granules.

SUMMARY OF THE INVENTION

The present inventors have found that rupture of a coating film of coated granules at the time of tablet compression can be decreased by compressing the granules at a temperature exceeding room temperature. Thus, the present invention has been completed.

That is, the present invention provides:

(1) A method of manufacturing a tablet, which comprises compressing coated granules containing a physiologically active substance at a temperature exceeding room temperature;

(2) The method according to the above (1), wherein the physiologically active substance is a physiologically active substance which is unstable to an acid;

(3) The method according to the above (2), wherein the physiologically active substance which is unstable to an acid is a proton pump inhibitor (PPI);

(4) The method according to the above (3), wherein the PPI is a benzimidazole compound or a salt thereof;

(5) The method according to the above (4), wherein the benzimidazole compound is lansoprazole or an optically active isomer thereof;

(6) The method according to the above (1), wherein the coated granules are enteric-coated granules;

(7) The method according to the above (6), wherein the enteric coating layer contains an aqueous enteric polymer base;

(8) The method according to the above (7), wherein the aqueous enteric polymer base is a methacrylic copolymer;

(9) The method according to the above (1), wherein the temperature exceeding room temperature is about 25° C. or higher;

(10) The method according to the above (1), wherein the temperature exceeding room temperature is a temperature of about 25° C. to about 50° C.;

(11) The method according to the above (1), wherein the temperature exceeding room temperature is a temperature of about 25° C. to about 40° C.;

(12) The method according to the above (1), wherein the tablet is an oral disintegrating tablet;

(13) A method for manufacturing an oral disintegrating tablet, which comprises compressing enteric-coated granules containing a physiologically active substance which is unstable to an acid, and warmed at about 25° C. to about 50° C.;

(14) The method according to the above (13), wherein a tablet compressing machine is warmed;

(15) The method according to the above (14), wherein the tablet compressing machine is a rotary tablet compressing machine, and compressing is performed after a rotary turn table thereof is warmed;

(16) A method of decreasing rupture of a coating film of coated granules containing a physiologically active substance, which comprises warming the coated granules to a temperature exceeding room temperature to compress the granules;

(17) A method of reducing the dissolved percentage in the acid stage of a tablet comprising coated granules containing a physiologically active substance, which comprises warming the coated granules to a temperature exceeding room temperature to compress the granules;

(18) A method of improving hardness of a tablet, which comprises warming coated granules containing a physiologically active substance to a temperature exceeding room temperature to compress the granules;

(19) A tablet obtainable by coating a composition containing a physiologically active substance with a coating layer, adding additive(s) to the resulting coated granules, warming a mixture of the coated granules and the additive(s) to a temperature exceeding room temperature, and compressing the mixture;

(20) The tablet according to the above (19), wherein the physiologically active substance is a physiologically active substance which is unstable to an acid;

(21) The tablet according to the above (20), wherein the physiologically active substance which is unstable to an acid is PPI of a benzimidazole compound or a salt thereof;

(22) The tablet according to the above (21), wherein the benzimidazole compound is lansoprazole or an optically active isomer thereof;

(23) A tablet obtained by the method according to the above (1);

(24) A tablet, wherein its dissolved percentage in the acid stage is improved by tablet compression under warming;

(25) A tablet, wherein its hardness is increased by tablet compression under warming;
(26) A tablet comprising coated granules, wherein rupture of a coating film of the coated granules is decreased by tablet compression under warming;
(27) A tablet comprising coated granules, wherein its dissolved percentage in the acid stage is about 10% or less, its hardness is improved, and rupture of a coating film of the coated granules is decreased;
(28) An enteric-coated granule which comprises lansoprazole or an optically active isomer, and is warmed to a temperature exceeding room temperature;
(29) The granule according to the above (28), wherein the enteric-coated layer comprises an aqueous enteric polymer base;
(30) The granule according to the above (28), wherein the aqueous enteric polymer base is a methacrylic copolymer;
(31) The granule according to the above (28), wherein the temperature exceeding room temperature is about 25° C. or higher;
(32) The granule according to the above (28), wherein the temperature exceeding room temperature is a temperature of about 25° C. to about 50° C.;
(33) The particle according to the above (30), wherein the temperature exceeding room temperature is a temperature of about 25° C. to about 40° C.;
(34) Use of an enteric-coated granule comprising a physiologically active substance which is unstable to an acid, and warmed to a temperature exceeding room temperature, for manufacturing a tablet having improved acid resistance; and the like.

DETAILED DESCRIPTION OF THE INVENTION

Figure 1:
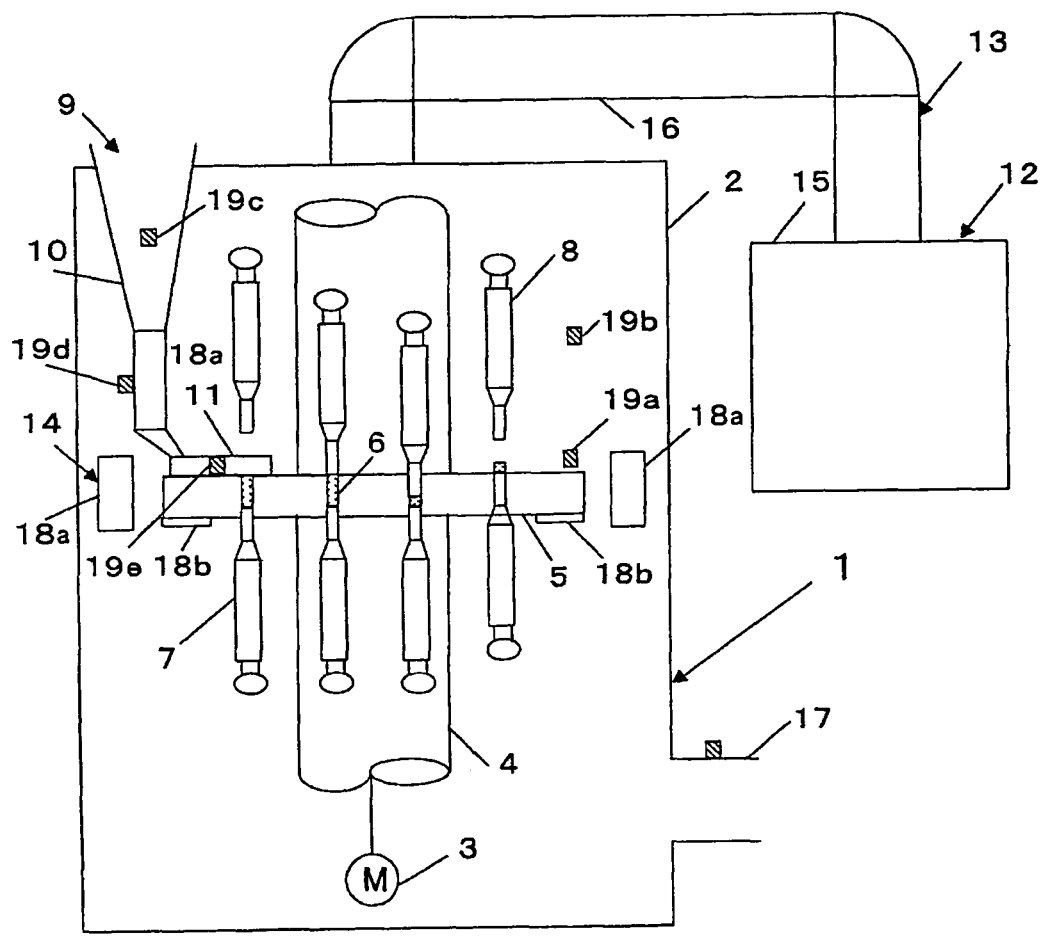
FIG. 1 illustrates a schematic configuration of a rotary tablet compressing machine which is one embodiment of the tablet compressing apparatus used in the present invention.

As used herein, the "coated granules" means that subject granules to be coated have been coated with a coating agent. Here, "coated" includes not only a case where a subject (granules) to be coated is completely coated, but also a case where a part of the subject is exposed.

The "physiologically active substance" contained in the "granules" is not particularly limited as far as it is preferably coated for the purpose of, for example, masking a taste or an odor, rendering soluble in intestines, or sustained release. Examples of the substance which is preferably coated include a physiologically active substance exhibiting bitterness, a physiologically active substance which is unstable to an acid, and the like.

The "physiologically active substance" may be any substance in the form of solids, powders, crystals, oils and solutions, and examples thereof to be used include one or more drug ingredients selected from nourishing and health-promoting agents, antipyretic-analgesic-antiinflammatory agents, antipsychotic drugs, antianxiety drugs, antidepressants, hypnotic-sedatives, spasmolytics, central nervous system affecting drugs, cerebral metabolism ameliolators, cerebral circulation ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, antidiabetic agents, drugs for osteoporosis, antirheumatics, skeletal muscle relaxants, antimotion sickness drugs, hormones, alkaloid narcotics, sulfa drugs, drugs for treatment of gout, anticoagulants, antimalignant tumor agents, agents for Alzheimer's disease, and the like. These physiologically active substances may be any of free compounds and salts thereof. Further, they may be racemic compounds or optically active compounds. Furthermore, they may be prodrugs thereof.

Examples of the nourishing and health-promoting agents include vitamins such as vitamin A, vitamin D, vitamin E (d-α-tocopherol acetate and the like), vitamin $B_1$ (dibenzoylthiamine, fursultiamine hydrochloride and the like), vitamin $B_2$ (riboflavin butyrate and the like), vitamin $B_6$ (pyridoxine hydrochloride and the like), vitamin C (ascorbic acid, sodium L-ascorbate and the like), vitamin $B_{12}$ (hydroxocobalamin acetate and the like) and the like; minerals such as calcium, magnesium and iron; amino acids; oligosaccharides; galenical; and the like.

Examples of the antipyretic-analgesic-antiinflammatory agents include aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serrapeptase, lysozyme hydrochloride, tolfenamic acid, mefenamic acid, diclofenac sodium, flufenamic acid, salicylamide, aminopyrine, ketoprofen, indomethacin, bucolome, pentazocine, and the like.

Examples of the antipsychotic drugs include chlorpromazine, reserpine, and the like.

Examples of the antianxiety drugs include alprazolam, chlordiazepoxide, diazepam, and the like.

Examples of the antidepressants include imipramine, maprotiline hydrochloride, amphetamine, and the like.

Examples of the hypnotic-sedatives include estazolam, nitrazepam, diazepam, perlapine, phenobarbital sodium, and the like.

Examples of the spasmolytics include scopolamine hydrobromide, diphenhydramine hydrochloride, papaverine hydrochloride, and the like.

Examples of the central nervous system affecting drugs include citicoline, and the like.

Examples of the cerebral metabolism ameliolators include meclofenoxate hydrochloride, and the like.

Examples of the cerebral circulation ameliolators include vinpocetine, and the like.

Examples of the antiepileptics include phenytoin, carbamazepine, and the like.

Examples of the sympathomimetic agents include isoproterenol hydrochloride, and the like.

Examples of the gastrointestinal function conditioning agents include stomachic-digestives such as diastase, saccharated pepsin, scopolia extract, cellulase AP3, lipase AP, cinnamon oil, etc.; intestinal function controlling drugs such as berberine chloride, resistant lactic acid bacterium, *Lactobacillus bifidus*, etc.; and the like.

Examples of the antacids include magnesium carbonate, sodium hydrogen carbonate, magnesium aluminometasilicate, synthetic hydrotalcite, precipitated calcium carbonate, magnesium oxide, and the like.

Examples of the antiulcer agents include PPI such as benzimidazole compounds or salts thereof, for example, lansoprazole, omeprazole, rabeprazole, pantoprazole, etc. (including respective optical active isomers); histamine $H_2$ receptor antagonists such as famotidine, cimetidine, ranitidine hydrochloride, etc.; and the like.

Examples of the antitussive-expectorants include chloperastine hydrochloride, dextromethorphan hydrobromide, theophylline, potassium guaiacolsulfonate, guaifenesin, codeine phosphate, and the like.

Examples of the antiemetics include diphenidol hydrochloride, metoclopramide, and the like.

Examples of the respiratory stimulants include levallorphan tatrate and the like.

Examples of the bronchodilators include theophylline, salbutamol sulfate, and the like.

Examples of the antiallergic agents include amlexanox, seratrodast, and the like.

Examples of the dental buccal drugs include oxytetracycline, triamcinolone acetonide, chlorhexidine hydrochloride, lidocaine, and the like.

Examples of the antihistamines include diphenhydramine hydrochloride, promethazine, isothipendyl hydrochloride, dl-chlorpheniramine maleate, and the like.

Examples of the cardiotonics include caffeine, digoxin, and the like.

Examples of the antiarryhythmic agents include procainamide hydrochloride, propranolol hydrochloride, pindolol, and the like.

Examples of the diuretics include isosorbide, furosemide, thiazide agents such as HCTZ, etc.; and the like.

Examples of the hypotensive agents include delapril hydrochloride, captopril, hexamethonium bromide, hydralazine hydrochloride, labetalol hydrochloride, manidipine hydrochloride, candesartan cilexetil, methyldopa, losartan, valsartan, eposartan, irbesartan, tasosartan, telmisartan, and the like.

Examples of the vasoconstrictors include phenylephrine hydrochloride, and the like.

Examples of the coronary vasodilators include carbocromen hydrochloride, molsidomine, verapamil hydrochloride, and the like.

Examples of the peripheral vasodilators include cinnarizine and the like.

Examples of the antihyperlipidemic agents include cerivastatin sodium, simvastatin, pravastatin sodium, and the like.

Examples of the cholagogues include dehydrocholic acid, trepibutone, and the like.

Examples of the antibiotics include cephem antibiotics such as cefalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefmenoxime hydrochloride, cefsluodin sodium, etc.; synthetic antibacterials such as ampicillin, cyclacillin, sulbenicillin sodium, nalidixic acid, enoxacin, etc.; monobactam antibiotics such as carumonam sodium; penem antibiotics; carbapenem antibiotics; and the like.

Examples of the chemotherapeutic agents include sulfamethizole hydrochloride, thiazosulfone, and the like.

Examples of the antidiabetic agents include tolbutamide, voglibose, pioglitazone hydrochloride, troglitazone, glibenclamide, troglitazone, rosiglitazone maleate, acarbose, miglitol, emiglitate, and the like.

Examples of the drugs for osteoporosis include ipriflavone, and the like.

Examples of the skeletal muscle relaxants include methocarbamol, and the like.

Examples of the antimotion sickness drugs include meclizine hydrochloride, dimenhydrinate, and the like.

Examples of the antirheumatics include methotrexate, bucillamine, and the like.

Examples of the hormones include riothyroinine sodium, dexamethasone sodium phosphate, prednisolone, oxendolone, leupororelin acetate, and the like.

Examples of the alkaloid narcotics include opium, morphine hydrochloride, ipecac, oxycodone hydrochloride, opium alkaloids hydrochlorides, cocaine hydrochloride, and the like.

Examples of the sulfa drugs include sulfamine, sulfisomidine, sulfamethizole, and the like.

Examples of the drugs for treatment of gout include allopurinol, colchicine, and the like.

Examples of the anticoagulants include dicoumarol, and the like.

Examples of the anti-malignant tumor agents include 5-fluorouracil, uracil, mitomycin, and the like.

Examples of the agents for Alzheimer's disease include idebenone, vinpocetine and the like.

Among the above drug ingredients, those preferably used are nourishing and health-promoting agents, antipyretic-analgesic-antiinflammatory agents, hypnotic-sedatives, central nervous system affecting drugs, gastrointestinal function conditioning agents, antiulcer agents, antitussive-expectorants, antiallergic agents, antiarrhythmic agents, diuretics, hypotensive agents, vasoconstrictors, coronary vasodilators, antihyperlipidemic agents, antidiabetic agents, drugs for osteoporosis, skeletal muscle relaxants, antimotion sickness drugs, and the like.

In the present invention, drug ingredients which are particularly preferably used are antiulcer agents such as lansoprazole, etc.; antidiabetic agents such as voglibose, pioglitazone hydrochloride, etc.; and hypotensive agents such as manidipine hydrochloride, candesartan cilexetil, etc.

Further, two or more kinds of these drug ingredients may be incorporated in the rapidly disintegrating solid preparation of the present invention.

The drug ingredients may be diluted with diluents generally used in medical and food fields. In addition, they may be those subjected to treatment for masking bitterness of the drug ingredients.

The above drug ingredients are used in an amount of, for example, 0.01 to 90 parts by weight, preferably 0.02 to 50 parts by weight, more preferably 0.05 to 30 parts by weight based on 100 parts by weight of the solid preparation.

As the above "physiologically active substance which is unstable to an acid", there are compounds which become unstable in an acidic region and/or are inactivated with an acid (in particular, drug ingredients), and specific examples thereof include PPI. Examples of PPI include benzimidazole compounds having the antiulcer activity or salts thereof (including racemic compounds and optically active isomers) (e.g., lansoprazole, omeprazole, rabeprazole, pantoprazole, perprazole, leminoprazole, TU-199, etc.). Among them, preferred PPI are lansoprazole, omeprazole, rabeprazole, pantoprazole, etc., and particularly preferred PPI are lansoprazole and an optically active isomer thereof. As the optically active isomer of lansoprazole, R-isomer is particularly preferable. In addition, examples of PPI include tenatoprazole.

The "granules" may contain binding agents, lubricants, excipients, etc., which are used in manufacturing the following general preparations, in addition to the physiologically active substance. The amounts thereof to be used are those used in manufacturing the general preparations. When the physiologically active substance is a "physiologically active substance which is unstable to an acid", it is preferable to incorporate a basic inorganic salt into the granules in order to stabilize the physiologically active substance in the preparations. Examples of the "basic inorganic salt" include basic inorganic salts of sodium, potassium, magnesium and/or calcium (e.g. sodium carbonate, sodium bicarbonate, potassium carbonate, potassium bicarbonate, ground magnesium carbonate, magnesium carbonate, magnesium oxide, magnesium hydroxide, etc.), and the like.

The "granules" are not particularly limited as far as they are in granular forms. They may have or may not have cores. In addition, when the granules have cores, the cores may contain, or may not contain the physiologically active substance. The particle diameter of granules may be determined according to that of the desired coated granules. The granules may be prepared by a per se known method or a similar method according to a particular form thereof.

When the granules do not have cores, they can be prepared by a per se known granulation method.

As the "granulation method", there are a tumbling granulation method (e.g. centrifugal tumbling granulation method), a fluidized granulation method (e.g. tumbling fluidized bed granulation, fluidized granulation etc.), an agitation granulation method, and the like. Among them, a fluidized granulation method is preferable. Particularly preferable is a tumbling fluidized bed granulation method.

Examples of the tumbling granulation method include a method using "CF apparatus" manufactured by Freund. Examples of the tumbling fluidized bed granulation method include a method using "Spiralflow", "Multiplex" manufactured by Powrex, or "Newmalme" manufactured by Fujipowdal. A spraying method of a mixture can be appropriately selected according to a particular kind of a granulation apparatus, and may be any of top spray system, bottom spray system, tangential spray system, etc. Among them, tangential spray system is preferable.

On the other hand, the granules having cores can be prepared by coating the cores with the physiologically active substance by a per se known method.

For example, according to the method described in JP 5-092918 A (coating method), granules can be prepared by coating cores containing crystalline cellulose and lactose with a physiologically active substance which is unstable to an acid and, if necessary, a basic inorganic salt, a binding agent, a lubricant, an excipient, a water-soluble polymer, etc. (hereinafter, sometimes, abbreviated as coated layer), and the like.

The average particle diameter of the "cores" is about 40 to 350 μm, preferably about 50 to 250 μm, more preferably about 100 to 250 μm, particularly preferably about 100 to 200 μm. Examples of the cores having such an average particle diameter include particles, 100% of which pass through No. 50 (300 μm) sieve, and in which particles remaining on No. 60 (250 μm) are about 5 w/w % or less of the whole, and particles passing through No. 282 (53 μm) are about 10 w/w % or less of the whole. The specific volume of the "cores" are 5 ml/g or less, preferably 4 ml/g or less, more preferably 3 ml/g or less.

Examples of the "cores" include (1) a spherical granulated product of crystalline cellulose and lactose, (2) a 150-250 μm spherical granulated product of crystalline cellulose (manufactured by Asahi Chemical industry Co., Ltd., Avicel SP), (3) a 50-250 μm agitation granulated product containing lactose (9 parts) and α starch (1 parts), (4) 250 μm or less finely divided particles obtained by classifying microcrystalline cellulose spherical granules described in JP 61-213201 A, (5) processed products such as waxes which are formed into spheres by spray chilling or melt cooling granulation, (6) a processed product such as a gelatin bead product of an oil component, (7) calcium silicate, (8) starch, (9) porous particles of chitin, cellulose, chitosan, etc., and (10) a bulk product such as granulated sager, crystalline lactose, crystalline cellulose, sodium chloride, etc., and preparation processed products thereof. Farther, these cores may be prepared by a per se known grinding method or granulation method, and passed through a sieve to prepare particles having the desires particle diameter.

Examples of the "spherical granulated product of crystalline cellulose and lactose" include (i) a 100-200 μm spherical granulated product containing crystalline cellulose (3 parts) and lactose (7 parts) (e.g., Nonparel 105 (70-140) (particle diameter 100 to 200 μm), manufactured by Freund) (ii) a 150-250 μm spherical granulated product containing crystalline cellulose (3 parts) and lactose (7 parts) (e.g., Nonparel NP-7:3, manufactured by Freund), (iii) a 100-200 μm spherical granulated product containing crystalline cellulose (4.5 parts) and lactose (5.5 parts) (e.g., Nonparel 105T (70-140) (particle diameter 100 to 200 μm), manufactured by Freund) etc.], (iv) a 150-250 μm spherical granulated product containing crystalline cellulose (5 parts) and lactose (5 parts) [e.g., Nonparen NP-5:5, manufactured by Freund], and the like.

In order to prepare a preparation, which is excellent in the solubility, while maintaining the suitable strength, preferred examples of the "cores" include a spherical granulated product containing crystalline cellulose and lactose, more preferably a spherical granulated product containing crystalline cellulose and lactose (containing about 50% or weight or more of lactose). A preferred product contains crystalline cellulose in an amount of about 20 to 50% by weight, preferably about 40 to 50% by weight and lactose in an amount of about 50 to 80% by weight, preferably about 50 to 60% by weight.

As the cores used in the present invention, a spherical granulated product of crystalline cellulose and lactose is preferable, and a 100-200 μm spherical granulated product containing crystalline cellulose (4.5 parts) and lactose (5.5 parts) is further preferable.

The "cores" may contain a physiologically active substance such as the aforementioned drug ingredients. However, since a coating layer containing the physiologically active substance can control release of the physiologically active substance, the cores may not contain any physiologically active substance.

The "cores" may be fine particles and, in order to decrease a variation in coating, it is preferable that the cores are as uniformly spherical as possible.

By coating the granules thus obtained with a coating agent by a per se known method, the "coated granules" are obtained. Examples of the coating agent include enteric polymers (e.g., cellulose acetate phthalate, methacrylic acid (hereinafter, referred to as methacrylic acid) copolymer L, methacrylic acid copolymer LD [Eudragit L30D-55 (trade name: manufactured by Rohm), methacrylic acid copolymer S, hydroxypropylmethylcellulose phthalate, hydroxymethylcellulose acetate succinate, hydroxypropylmethylcellulose acetate succinate, carboxymethylethylcellulose, Colicoat MAE30DP (trade name; manufactured by BASF), Polykid PA30 (trade name: manufactured by Sanyo Chemical Industries, Ltd.) etc.], carboxymethylethylcellulose, shellac, methacrylic acid copolymer [e.g. Eudragit NE30D (trade name), Eudragit RL30D (trade name), Eudragit RS30D (trade name), etc.], triethyl citrate, polyethylene glycol, acetylated monoglyceride, triacetin, castor oil, etc.), polymers soluble in stomach (e.g., polyvinyl acetal diethylaminoacetate, aminoalkyl methacrylate copolymer, etc.), water-soluble polymers (e.g., hydroxypropylcellulose, hydroxypropylmethylcellulose, etc.), slightly soluble polymers (e.g. ethylcellulose, aminoalkyl methacrylate copolymer RS, ethyl acrylate-methyl methacrylate copolymer etc.), waxes, and the like. These may be used alone, or two or more of them may be used by mixing.

As the preferred coating agent for enteric coating, there are coating agents containing an aqueous enteric polymer base such as cellulose acetate phthalate (CAP), hydroxypropylmethylcellulose phthalate (hereinafter, described as HP-55), hydroxymethylcellulose acetate succinate, methacrylic acid copolymer [e.g. Eudragit L30D-55, Colicoat MAE30DP, Polykid PA30, etc.], carboxymethylethylcellulose, shellac, and the like are preferable. The preferable aqueous enteric polymer base is a methacrylic acid copolymer.

The coating layer may be composed of plural layers. For example, there is a method of coating granules with an enteric coating layer containing a methacrylic acid copolymer and polyethylene glycol, coating the resultant granules with an enteric coating layer containing a methacrylic acid copolymer and triethyl citrate and further coating the resultant granules with an enteric coating layer containing a methacrylic acid copolymer and polyethylene glycol. Further, for example, in order to improving the strength of a tablet, an enteric coating layer may be overcoated with a water-soluble sugar alcohol such as mannitol and the like.

Preferably, an enteric coating layer is a layer of 10 to 100 µm, preferably 20 to 70 µm, more preferably 30 to 50 µm in thickness, which coats the whole surface of a composition containing the physiologically active substance. Therefore, as the particle diameter of the coated granules is smaller, weight % of the enteric coating layer occupied in the whole coated granules becomes larger. Usually, the enteric coating layer is 20 to 90% by weight, preferably 30 to 70% by weight, more preferably 50 to 70% by weight based on the whole coated granules.

The particle diameter of the coated granules is not particularly limited, but fine granules or granules are preferable and, in the case of an oral rapidly disintegrating tablet, the average particle diameter thereof is about 400 µm or less so as to avoid rough mouthfeel and a feeling of disorder. The preferred average particle diameter is 200 to 400 µm, and a further preferred average particle diameter is 300 to 400 µm.

As the "coated granules", fine granules described in JP 2000-281564 A and JP 2000-103731 A are particularly preferable.

In the method of manufacturing a tablet of the present invention, the coated granules alone may be compressed, but preferably, the coated granules and additive(s) are mixed, followed by compressing. At this time, the additive(s) may be granulated in advance, followed by mixing. As the additives, those used in manufacturing general preparations may be used, and the amounts thereof to be added are those used in manufacturing general preparations.

As the "additive(s)" to be used, there are, for example, water-soluble sugar alcohol, crystalline cellulose, low-substituted hydroxypropylcellulose, and the like and, further, the additive(s) to be used include binding agents, acidulants, foaming agents, artificial sweeteners, flavors, lubricants, coloring agents, stabilizers, excipients, disintegrants, and the like.

The "water-soluble sugar alcohol" means sugar alcohol which requires less than 30 ml of water to dissolve it, when 1 g of the sugar alcohol is added to water, and the sugar alcohol is dissolved within about 30 minutes by strongly shaking at 20° C. for 30 seconds every 5 minutes.

Examples of the "water-soluble sugar alcohol" include sorbitol, mannitol, maltitol, reduced starch saccharified product, xylitol, reduced palatinose, erythritol, and the like. These may be used by mixing two or more kinds of them at an appropriate ratio.

Examples of the "water-soluble sugar alcohol" include preferably mannitol, xylitol and erythritol, further preferably mannitol and erythritol, particularly preferably mannitol. Erythritol which is usually used is that produced by fermentation with yeast, etc., using glucose as a raw material and having a particle size of 50 mesh or smaller. Such erythritol is available as a commercial product [Nikenkagaku (K.K.) etc.].

In case of an oral disintegrating agent, in order to obtain sufficient preparation strength and a sufficient oral disintegrating property, the "water-soluble sugar alcohol" is used usually in an amount of about 5 to 97 parts by weight, preferably about 10 to 90 parts by weight, more preferably about 20 to 80 parts by weight based on 100 parts by weight of a total of additives.

In case of mannitol or erythritol, desirably, it may be contained usually at about 5 to 90 parts by weight, preferably about 10 to 80 parts by weight, more preferably about 20 to 80 parts by weight, most preferably about 50 to 80 parts by weight based on 100 parts by weight of a total of additives.

The "crystalline cellulose" is not specifically limited as far as it is obtained by partially depolymerizing and purifying α-cellulose. In addition, the crystalline cellulose includes cellulose called microcrystalline cellulose. Examples of the crystalline cellulose include Ceolas KG 801, Avicel PH 101, Avicel PH 102, Avicel PH 301, Avicel PH 302, Avicel RC-591 (crystalline cellulose-sodium carmelose), and the like. Preferable examples thereof include Ceolus KG 801 called high compactible Avicel. These crystalline celluloses may be used alone, or in combination two or more thereof. These crystalline celluloses are available as commercial products [manufactured by Asahi Chemical Industry Co., Ltd.].

The crystalline cellulose may be incorporated at about 3 to 50 parts by weight, preferably about 5 to 40 parts by weight, most preferably about 5 to 20 parts by weight based on 100 parts by weight of a total of additives.

The "low-substituted hydroxylpropylcellulose" means low-substituted hydroxypropylcellulose in which a content of a hydroxypropoxyl group (hereinafter, sometimes, abbreviated as HPC group content) in the hydroxypropylcellulose is about 5.0 to 9.9% by weight, inter alia, low-substituted hydroxypropylcellulose in which the HPC group content is about 5.0 to 7.0% by weight, low-substituted hydroxypropylcellulose in which the HPC group content is about 7.0 to 9.9% by weight, etc.

Examples of the low-substituted hydroxypropylcellulose in which the HPC group content is about 7.0 to 9.9% include LH-22, LH-32 and a mixture thereof, and these are available as a commercial product [manufactured by Shin-Etsu Chemical Co., Ltd.]. Alternatively, they may be prepared by a per se known method, for example, the method described in JP 57-53100 B disclosed hereinafter, or a similar method.

Examples of the low-substituted hydroxypropylcellulose in which the HPC group content is about 5.0 to 7.0% include LH-23, LH-33 and a mixture thereof described in Reference Examples hereinafter. These can be prepared by a per se known method, for example, the method described in JP 57-53100 B, or a similar method.

The particle diameter of the "low-substituted hydroxylpropylcellulose in which a content of a hydroxypropoxyl group is 5.0 to 7.0% by weight" is, for example, about 5 to 60 µm, preferably about 7 to 50 µm, more preferably about 10 to 40 µm as an average particle diameter.

Among such range, when L-HPC having a relatively large particle diameter (e.g., L-HPC having an average particle diameter of about 26 to 40 µm) is used, a preparation having an excellent disintegrating property can be prepared. On the other hand, when L-HPC having a relatively small particle diameter (e.g., L-HPC having an average particle diameter of about 10 to 25 µm) is used, a preparation having excellent preparation strength can be prepared. Therefore, a particle diameter of L-HPC can be appropriately selected depending on the properties of the desired preparation.

In case of an oral disintegrating tablet, in order to obtain a sufficient oral disintegrating property and sufficient preparation strength, the low-substituted hydroxypropylcellulose in which the HPC group content is 5.0 to 7.0% by weight or the low-substituted hydroxypropylcellulose in which the HPC group content is 7.0 to 9.9% is used usually at about 3 to 50 parts by weight, preferably about 5 to 40 parts by weight, further preferably 5 to 20 parts by weight based on 100 parts by weight of a total of additives.

Examples of the "binding agent" include hydroxypropylcellulose, hydroxypropylmethylcellulose, crystalline cellulose, α starch, polyvinylpyrrolidone, gum arabic powder, gelatin, pullulan, low-substituted hydropropylcellulose, and the like. When crystalline cellulose is used as the binding agent, a solid preparation having further higher preparation strength can be obtained, while maintaining the excellent oral disintegrating property.

Examples of the "acidulant" include citric acid (citric acid anhydride), tartaric acid, malic acid, and the like.

Examples of the "foaming agent" include sodium bicarbonate, and the like.

Example of the "artificial sweetener" include saccharine sodium, glycyrrhizin dipotassium, aspartame, stevia, somatin, and the like.

The "flavor" may be synthetic and natural ones, and examples thereof include lemon, lime, orange, menthol, strawberry, and the like.

Examples of the "lubricant" include magnesium stearate, sucrose fatty acid ester, polyethylene glycol, talc, stearic acid, and the like.

Examples of the "coloring agent" include edible pigments such as edible Yellow No. 5, edible Red No. 2, and edible Blue No. 2; edible lake pigments; red iron oxide; and the like.

Examples of the "stabilizing agent" include the aforementioned basic inorganic salts, and the like.

Examples of the "excipient" include lactose, sucrose, D-mannitol, starch, corn starch, crystalline cellulose, light silisic acid anhydride, titanium dioxide, and the like.

As the "disintegrating agent", there are disintegrating agents which are conventionally used in the field of pharmacy can be used, and examples thereof include (1) crosspovidone, (2) disintegrating agents called superdisintegrating agnet such as crosscarmelose sodium (FMC-manufactured by Asahi Chemical Industry Co., Ltd.), and carmelose calcium (Gotokuyakuhin), (3) carboxymethylstarch sodium (e.g. manufactured by Matsutani Chemical Industry Co., Ltd.), (4) low-substituted hydroxypropylcellulose (e.g. manufactured by Shin-Etsu Chemical Co., Ltd.), (5) corn starch, and the like. A particularly preferable disintegrating agent is, for example, crosspovidone.

The "crosspovidone" may be any of cross-linked polymers having a chemical name of 1-ethenyl-2-pyrrolidinone homopolymer including those called polyvinyl polypyrrodione (PVPP) and 1-vinyl-2-pyrolidinone homopolymer, and examples thereof include Corridone CL (manufactured by BASF), Polyplasdone XL (manufactured by ISP), Polyplasdone XL-10 (manufactured by ISP), Polyplasdone INF-10 (manufactured by ISP), and the like. Usually, the molecular weight thereof exceeds 1,000,000.

These disintegrating agents may be used alone, or in a combination of two or more thereof. For example, crosspovidone may be used alone, or in a combination of crosspovidone and another disintegrating agent.

Such the disintegrating agent is contained usually in an amount of 1 to 15 parts by weight, preferably about 1 to 10 parts by weight, more preferably about 3 to 7 parts by weight based on 100 parts by weight of a total of additives in an oral disintegrating tablet.

The method of manufacturing a tablet of the present invention is characterized in that coated granules at a temperature exceeding room temperature are compressed. In the present specification, sometimes, compression of a raw material powder or granules heated at a temperature exceeding room temperature like this is simply referred to as "compression under warming". "Room temperature" used herein refers to a temperature in a room at which compression is performed in manufacturing of a normal tablet, and the temperature usually refers to as about 20° C. to about 23° C. That is, a "temperature exceeding room temperature" refers to a temperature exceeding this temperature, and a lower limit may be preferably about 25° C. The temperature varies depending on a coating agent, a raw material powder or granules and the like to be used, but usually the temperature is preferably about 25° C. to about 50° C., further preferably about 25° C. to about 40° C. The temperature can be changed depending on the quality of the desired tablet. For example, when the dissolved percentage in the acid stage of the tablet obtained by the present method exceeds the desired numerical value, it is enough to raise a temperature of coated granules.

A method of bringing a temperature of coated granules to a temperature exceeding room temperature is not particularly limited. For example, coated granules may be directly warmed with a non-contact infrared heater or warm air, a contact resistance heater, or the like. Alternatively, coated granules may be indirectly warmed by a method of warming an entire compressing machine or a part of a compressing machine with which coated granules come into contact (e.g. turn table (rotating disk) of a rotary compressing machine), a method of warming a small chamber in which a compressing machine is disposed, or a method of warming a small chamber which partially covers a mortar and a pestle for compression and a granule feeding part. Warming of a small chamber can be performed, for example, by supplying warm air. Alternatively, both of coated granules and a compressing machine or a part thereof, or coated granules and a small chamber in which the granules are disposed may be warmed. When coated granules to be subjected to compressing or a part or the whole of a compressing machine is warmed, it is generally preferable to warm a part with which coated granules directly come into contact (e.g. rotating disk, pestle) in a non-contact manner. However, a part with which coated granules do not come into contact directly is also effectively warmed with a contact resistance heater. A part with which coated granules do not come into contact directly means a back of a rotating disk, an upper pestle holder, a lower pestle holder, or the like. Alternatively, a compressing machine may be warmed by operating the compressing machine in advance in an unloaded state. Further, if a temperature of a compressing machine is risen by continuous operation and, at the same time, a compressing machine undergoes the influence of an external temperature, it is preferable to adjust the temperature of the compressing machine to the aforementioned temperature by appropriately disposing a sensor on a compressing machine or a small chamber in which a machine is disposed.

As an apparatus for manufacturing such a tablet, any apparatus for manufacturing a tablet provided with a temperature controlling part for maintaining a temperature of coated granules upon compressing at a predetermined temperature may be used and, for example, the following apparatus is suitable.

A suitable embodiment of the present invention will be illustrated by referring to the attached drawings. FIG. 1 illustrates a schematic configuration of a rotary tablet compressing machine 1 which is one embodiment of the tablet compressing apparatus used in the present invention. However, the tablet compressing apparatus of the present invention is not limited to this rotary compressing machine. The compressing machine 1 has a compressing chamber (housing) 2 which is constructed by combining transparent plate materials. In the compressing chamber 2, a vertical rotating axis 4 which is driving-bound to a motor 3 is disposed. The rotating axis supports a turn table 5, and the rotating axis 4 and the turn table 5 are rotated at a fixed rate in a predetermined direction based on driving of the motor 3.

On the turn table 5, plural compressing cells (mortars) 6 penetrating through the turn table 5 and extending parallel with the rotating axis 4 are formed at intervals on a circle of a predetermined radius having a center of the rotating axis 4. Below each compressing cell 6, there is disposed a lower compressing rod (pestle) 7 having an upper part of the approximately same external diameter as an internal diameter of this compressing cell 6. Each lower compressing rod 7 is supported by an up and down mechanism (not shown) which rotates with rotation of the rotating axis 4, and moves between a most fallen position (a position at which an upper end part of a rod is most fallen within a compressing cell) and a most risen position (a position at which an upper end part of a rod is projected upwardly from a compressing cell), during one turn of the turn table 5, depending on a rotation position, and based on driving of the motor 3.

Above each compressing cell 6, there is disposed an upper compressing rod (pestle 8). Each upper compressing rod 8 is supported by an up and down mechanism (not shown) which rotates with rotation of the rotating axis 4, and moves between a most fallen position (a position at which a lower end part of a rod is most fallen in a compressing cell) and a most risen position (a position at which a lower end part of a rod is escaped upwards from a compressing shell), during one turn of turn table 5, depending on a rotation position, and depending on driving of motor 3. In addition, a lower end part of each upper compressing rod 8 have the approximately same external diameter as an internal diameter of a compressing cell 6, and can press a powder to be compressed from upper and lower directions to mold a tablet in a compressing cell 6, in conjunction with an upper end part of a lower compressing rod 7.

For feeding a powder to be compressed to each compressing cell 6 and filling the powder into the cell, the compressing machine 1 is further provided with a powder feeding apparatus 9. For example, this powder feeding apparatus 1 is provided with a powder feeding hopper 10 which falling-supplies a powder onto the turn table 5, and a feeder 11 which guides a powder to be suppressed which have been supplied from this hopper 10 to the turn table 5, to each compressing cell 6.

According to the compressing machine 1 providing with the above configuration, a powder to be compressed is falling-supplied from the hopper 11 onto the turn table 5. A powder on the turn table 5 is introduced to each compressing cell 6 by the feeder 11, based on rotation of this turn table 5. While a powder is filled into the compressing cell 6, a lower compressing rod 7 is at a most fallen position, whereby, a predetermined amount of a powder is filled into each compressing cell 6. Then, a lower end part of an upper compressing rod 8 is inserted into the compressing cell 6 with a predetermined amount of a powder filled therein, from an upper direction. At the same time, a lower compressing rod 7 is risen. As a result, the powder in the compressing cell 6 is compressed between the lower compressing rod 7 and the upper compressing rod 8 and is molded into a tablet. After molding of a tablet, the upper compressing rod 8 is escaped upwards from the compressing cell 6. And, the molded tablet is pushed out from the compressing cell 6 by elevation of the lower compressing rod 7, and is recovered in a tray (not shown) provided at an external periphery of the turn table 5.

Then, an apparatus for warming the compressing machine 1 will be illustrated. A warming apparatus 12 maintains a powder to be compressed (a mixed powder of a fine granular main drug and an excipient powder) at a predetermined temperature or in a predetermined range of a temperature before or during manufacturing of a tablet with a compressing machine 1. For this purpose, in this embodiment, the warming apparatus 12 is provided with a warm air heater 13 and a radiation heater (contact-type and non-contact-type heaters) 14. The warm air heater 13 is provided with a warm air generator 15, an insulating air supplying duct 16 which guides the warm air generated in this warm air generator 15 to the compressing chamber 2, and an evacuating duct 17 for introducing the air in the compressing chamber 2 to the outside. On the other hand, the radiation heater 14 has one or plural non-contact-type heater(s) (e.g. infrared heater 18a) which is (are) disposed in the interior of the compressing chamber 2, in particular, in the vicinity of the turn table 5 without coming into contact with the turn table, and a contact-type heater (e.g. resistance heater 18b) provided in contact with an underside or an external peripheral surface of the turn table 5. It is preferable that these non-contact-type heater 18a and contact-type heater 18b are detachable, and can be removed from the compressing chamber 2 when they are not necessary.

For controlling the warming apparatus 12, plural temperature detectors 19 (19a to 19e) are disposed in the compressing chamber 2. As a position at which the temperature detector 19 is disposed, for example, one or more places of the surfaces of the turn table 5, the hopper 10, the air supplying duct 16 and the evacuating duct 17 or the vicinities thereof are preferable. However, a position at which the temperature detector is disposed is not limited to specific places as far as a temperature of a powder to be compressed or a temperature of the turn table 5 can be directly or indirectly detected.

Figure 2:
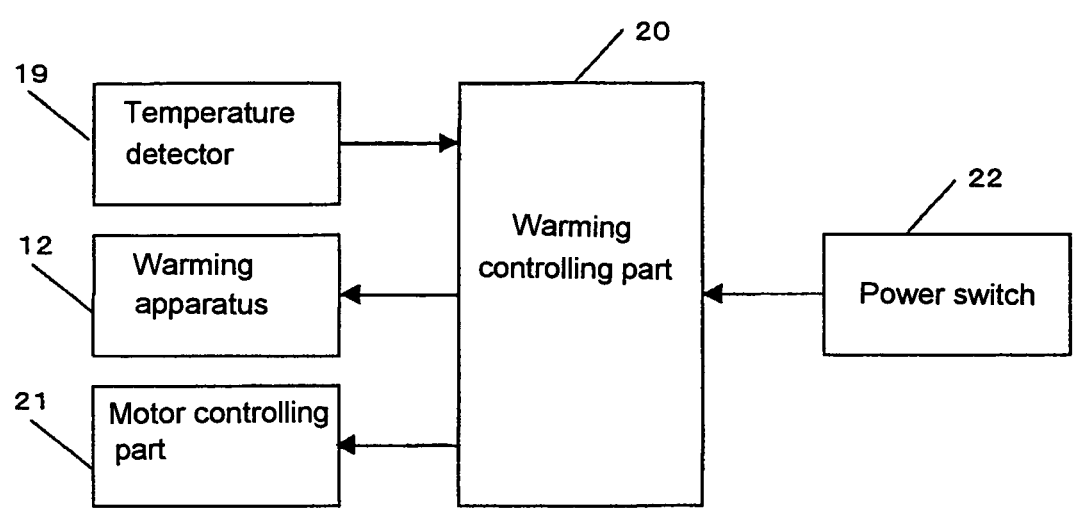
FIG. 2 illustrates a schematic block diagram for controlling a warming device of the apparatus of FIG. 1.

As shown in FIG. 2, a warming controlling part 20 which controls the warming apparatus 12 is electrically connected to the aforementioned warm air generator 15, warming apparatus 12 such as non-contact-type infrared heater 18a and contact-type resistance heater 18b, plural temperature detectors 19, compressing machine driving motor controlling part 21 and power switch 22.

Figure 3:
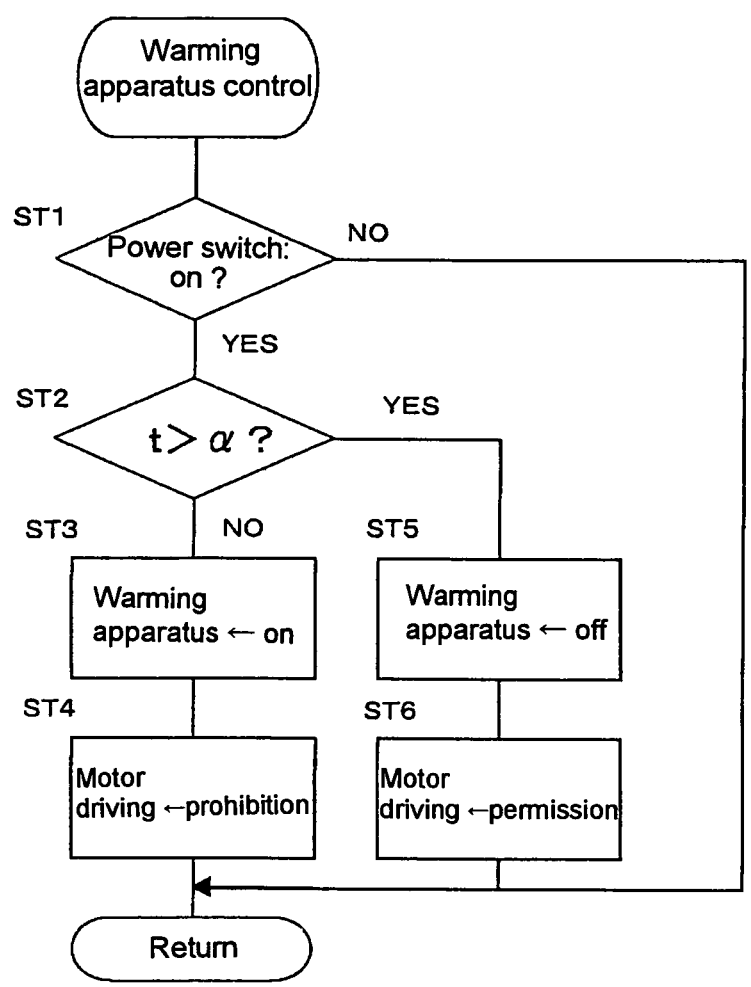
FIG. 3 illustrates a program for actuating the warming device of FIG. 2.

The thus constructed warming controlling part 20 is operated based on a program shown in FIG. 3. This program is a subroutine of a main program which manages the whole of the compressing machine 1, and is executed repeatedly at a fixed time which is timer-set by the main program. Specifically, the warming controlling part 20 determines first whether a power switch 22 is switched on or not (ST1). When the power switch 22 is switched off, the program stands ready. When the power switch 22 is switched on, whether a detection temperature t of the temperature detector 19 exceeds a predetermined standard temperature α or not is determined (ST2).

The standard temperature α varies depending on a detection site (subject) of the temperature detector 19, and can be set depending on each sensor. For example, when the temperature detector 19 detects an ambient temperature (room temperature) of the compressing chamber 2, the standard temperature α is set, for example, at 25° C. However, the standard temperature is not limited to that value, but for example, can be set at a suitable value in a range of about 25° C. to about 50° C. On the other hand, when the temperature detector 19 detects a temperature of the surface of the turn table 5 or a temperature of a site with which a powder to be compressed comes into contact, the standard temperature is set at an arbitrary value of about 30° C. to about 40° C.

When a detection temperature t is not higher than the standard temperature, the warming apparatus 12 is switched on (ST3), and driving of the motor 3 is prohibited via the compressing machine driving motor controlling part 21 (ST4). As a result, until a temperature of a powder to be compressed before compression becomes not lower than the standard temperature, the compressing apparatus stands ready. On the other hand, when a powder to be compressed is sufficiently warmed by the warming apparatus 12 and a detection temperature "t" exceeds the standard temperature, the warming apparatus 12 is switched off (ST5), and driving of the motor 3 is permitted via the compressing machine driving motor controlling part 21 (ST6).

In addition, a temperature may be controlled based on an output of the sensor also during compression. However, during compression, when a temperature of a powder to be compressed can be maintained at not lower than the predetermined standard temperature by the heat produced in the apparatus, control of a lower limit temperature is not necessary after initiation of compression.

The tablet of the present invention can be prepared by a conventional method in the field of pharmacy except that coated granules at a temperature exceeding room temperature are compressed. For example, there is a method of mixing coated granules, optionally, additive(s) and water, compressing the mixture and, optionally, drying it.

"Mixing" is performed by a generally used mixing method such as mixing, kneading, granulation, etc. The "mixing" is performed by using an apparatus such as a vertical granulator VG10 (manufactured by Powlech), a universal kneader (manufactured by Hatatekosho), a fluidized bed granulator LAB-1, FD-3S (manufactured by Powlech), a V-type mixer, a tumbler mixer, etc.

"Compression" is performed by compression at a pressure of 1 to 80 kN/cm$^2$, 5 to 50 kN/cm$^2$, preferably 15 to 40 kN/cm$^2$ using a single compressing machine (manufactured by Kikusuiseisakusho) or a rotary compressing machine (manufactured by Kikusuiseisakusho). In addition, in the rotary compressing machine, compression may be performed at a normal rotation speed, for example, 3 to 120 min$^{-1}$, preferably 3 to 80 min$^{-1}$, more preferably 5 to 60 min$^{-1}$.

"Drying" may be performed by any method which is used for drying in general pharmacy, such as vacuum drying and fluidized bed drying.

In the thus obtained tablet of the present invention, rupture of a coating film of coated granules is decreased. For example, in case of a tablet containing a physiologically active substance which is unstable to an acid in coated granules, an dissolution rate in an acidic solution, that is, the dissolved percentage in the acid stage is decreased even in the tablet which is prepared at normal pressure and rotation speed using a rotary compressing machine. Depending on a coating agent to be used, the rate can be usually decreased to about 10% or smaller, further about 7% or smaller. Depending on ingredients to be used, a further suitable dissolved percentage in the acid stage is about 5% or smaller, more preferably about 3% or smaller. Most preferably, it is possible to decrease the rate to about 1% or smaller. Herein, the dissolved percentage in the acid stage is obtained by performing a dissolution test for 1 hour using 0.1 N HCl 500 mL (75 rpm), collecting the dissolved solution, filtering the solution with a 0.45 μm membrane filter, measuring the absorbance and calculating a dissolution rate of a drug into 0.1 N HCl according to Japanese Pharmacopoeia, Dissolution Test, the Second Method. In addition, the tablet obtained by compression under warming of the present invention has improved hardness as compared with a tablet obtained by compressing a powder or granules at room temperature. As such tablet, not only when coated granules are used as a raw material, but also when a normal powder or granules are used, a tablet with improved hardness is obtained. Herein, hardness of a tablet is an index showing hardness of a tablet, and usually refers to a compression force when a tablet is ruptured by compressing in a diameter direction. Hardness depends on a size of a tablet and a compression pressure and, according to the present invention, even at a normal compression pressure, hardness of about 10 to 300 N can be achieved. When the above coated granules are subjected to compression under warming, a tablet in which both of the dissolved percentage in the acid stage and hardness are improved is obtained. For example, hardness of usually about 10 to 200 N, preferably about 15 to 80 N can be achieved. For example, in case of an oral disintegrating tablet containing enteric coated granules of a diameter of 9 mm which belongs to a tablet of the lowest hardness, according to the present invention, hardness of about 10 to 50 N, preferably about 15 to 40 N, more preferably 20 to 35 N is obtained at a normal completion pressure. Therefore, in order to maintain the desired dissolved stage in the acid stage, and strength and hardness of a coating film, it is not necessary to increase a pressure or decrease a rotation speed, and a tablet having the desired properties can be prepared without lowering the production efficacy.

The tablet obtained by the method of the present invention can be taken in a similar manner as that of a normal tablet. For example, in case of an oral disintegrating tablet, it may be taken by chewing and swallowing without water, etc.

In addition, a dose of the tablet varies depending on a particular drug ingredient, an administration subject, a kind of disease, and the like, and may be selected form such a range that a dose as a drug ingredient becomes an effective amount. For example, when a drug ingredient is lansoprazole, the rapidly disintegrating solid preparation of the present invention is useful for treatment and/or prevention of peptic ulcer (e.g. gastric ulcer, duodenal ulcer, stomal ulcer, Zollinger Ellison syndrome etc.), gastritis, reflux esophagitis, symptomatic Gastroesophageal Reflux disease (symptomatic GERD), etc.; removing *H. pylori*; suppression of upper digestive tract bleeding due to peptic ulcer, acute stress ulcer or bleeding gastritis; suppression of upper digestive tract bleeding due to invasive stress (stress resulting from big operation requiring concentrated management after operation, or cerebrovascular disorder, head trauma, multi-organ failure, extended burn); treatment and/or prevention of ulcer derived from a non-steroidal anti-inflammatory drug; administration before anesthesia; etc., and a dose thereof is 0.5 to 1500 mg/day, preferably 5 to 500 mg/day, more preferably 5 to 150 mg/day as lansoprazole per an adult (weighing 60 kg). Alternatively, lansoprazole may be used together with other drug(s) (anti-tumor agent, antibacterial agent etc.). Inter alia, by using together with an erythromycin antibiotic (e.g. clarithromycin, etc.) and a penicillin antibiotic (e.g. amoxicillin, etc.), an excellent effect can be obtained in removal of *H. pylori*.

When a drug ingredient is voglibose, the tablet of the present invention is effective for treating and preventing obesity, adiposis, hyperlipemia, diabetes, and the like, and a dose thereof is 0.01 to 30 mg/day, preferably 0.01 to 10 mg/day, more preferably 0.1 to 3 mg/day as voglibose per an adult (weighing 60 kg). The tablet may be administered once per day or by dividing into two or three times per day.

EXAMPLES

The present invention will be illustrated in more detail below by way of Examples and Reference Examples, but the present invention is not limited by them.

The physical properties of tablets obtained in Examples were measured by the following test method.

Hardness Test

Hardness was measured using a hardness tester (manufactured by Toyamasangyo (K.K.)). The test was performed ten times, and an average thereof is shown. Dissolved percentage in acid stage: dissolution rate with 0.1 N HCl.

A dissolution test was performed for 1 hour with 500 mL of 0.1 N HCl (75 rpm) according to Japanese Pharmacopoeia, Dissolution Test, the Second Method, the dissolved solution was collected, and filtered with a 0.45 μm membrane filter, the absorbance was measured, and the dissolution rate of a drug into 0.1 N HCl was calculated.

Example 1

(1) Preparation of Core-Containing Powder

Nonparel 105 (trade name; particle diameter: 100 to 200 μm; 41.58 kg) was placed in a tumbling fluidized type coating granulator [manufactured by Powrex, MP-400 type], an inlet air temperature was controlled so that an outlet air temperature at the stationary state became about 31° C., and a pre-prepared bulk solution having the following composition was spray-coated at a feeding rate of 1.4 kg/min by a tangential spraying manner. A prescribed amount (257.6 kg) of the bulk solution was sprayed, and then, the following (2) Preparation of undercoated film coated core-containing powder was performed.

| [Bulk solution] | |
|---|---|
| Lansoprazole | 39.6 kg |
| Magnesium carbonate | 13.2 kg |
| Low-substituted hydroxypropylcellulose LH-32 (Hydroxypropoxyl group content: 8.8% by weight) | 6.6 kg |
| Hydroxypropylcellulose (type SL) | 13.2 kg |
| Purified water | 185 L |

(2) Preparation of Undercoating Film Coated Core-Containing Powder

Following the aforementioned (1) Preparation of core-containing powder, an inlet air temperature was controlled so that an outlet air temperature at the stationary state became about 41° C., and a pre-prepared undercoating film solution having the following composition was sprayed at a feeding rate of 1.2 kg/min by a tangential spraying manner. A prescribed amount (132.0 kg) of the film solution was sprayed and, at that time, spraying was stopped, drying was performed as it was for about 11 minutes, the material was sieved by a No. 42 round sieve (350 μm) and No. 100 round sieve (150 μm) to obtain an undercoating film coated core-containing powder (132 kg).

| [Undercoating film solution] | |
|---|---|
| Hydroxypropylmethylcellulose (Type 2910, viscosity; 3 centistoke) | 9.24 kg |
| Titanium dioxide (TiO$_2$) | 3.96 kg |
| Sterilized talc [manufactured by Matsumurasangyo (K.K.)] | 3.96 kg |
| Low-substituted hydroxypropylcellulose LH-32 (Hydroxypropoxyl group content: 8.8% by weight) | 6.6 kg |
| Mannitol | 9.24 kg |
| Purified water | 99.0 L |

(3) Preparation of Enteric Core-Containing Powder

The aforementioned (2) undercoating film coated core-containing powder (44.0 kg) was placed in a tumbling fluidized-type coating granulator [manufactured by Powlech, MP-400 type], an inlet air temperature was controlled so that an outlet air temperature at the stationary state became about 42° C., and a prescribed amount (54.6 kg) of a pre-prepared enteric film solution (A) having the following composition was sprayed at a feeding rate of 1.05 kg/min by a tangential spraying manner.

| [Enteric film solution (A)] | |
|---|---|
| Eudragit L30D-55 | 32.05 kg |
| Eudragit NE30D | 3.570 kg |
| Polyethylene glycol 6000 | 1.071 kg |
| Monostearic acid glycerin | 0.629 kg |
| Polysorbate 80 | 0.189 kg |
| Iron sesquioxide | 0.006 kg |
| Yellow iron sesquioxide | 0.006 kg |
| Citric acid anhydride | 0.013 kg |
| Purified water | 44.3 L |

Subsequently, an inlet air temperature was controlled so that an outlet air temperature at the stationary state became about 42° C., and a prescribed amount (201.6 kg) of a pre-prepared enteric film solution (B) having the following composition was sprayed at a feeding rate of 1.00 kg/min by a tangential spraying manner.

| [Enteric film solution (B)] | |
|---|---|
| Eudragit L30D-55 | 117.6 kg |
| Eudragit NE30D | 13.06 kg |
| Triethyl citrate | 7.854 kg |
| Monostearic acid glycerin | 2.521 kg |
| Polysorbate 80 | 0.756 kg |
| Iron sesquioxide | 0.025 kg |
| Yellow iron sesquioxide | 0.025 kg |
| Citric acid anhydride | 0.021 kg |
| Purified water | 59.7 L |

Subsequently, an inlet air temperature was controlled so that an outlet air temperature at the stationary state became about 42° C., and a prescribed amount (27.3 kg) of the pre-prepared enteric film solution (A) having the above composition was sprayed at a feeding rate of 1.05 kg/min by a tangential spraying manner.

(4) Preparation of Enteric Core-Containing Powder Overcoated with Mannitol

Following the above (3), an inlet air temperature was controlled so that an outlet air temperature at the stationary state became about 42° C., and a pre-prepared film solution having the following composition was sprayed at a feeding rate of 0.64 kg/min by a tangential spraying manner. A prescribed amount (29.4 kg) thereof was sprayed and, at that time, spraying was stopped, drying was continued as it was and, after an outlet air temperature reached 65° C., the material was cooled. This was sieved by a No. 35 round sieve (420 μm) and a No. 60 round sieve (250 μm) to obtain an overcoated enteric core-containing powder (106 kg).

An average particle diameter of the resulting overcoated enteric core-containing powder was 340 μm.

| [Film solution] | |
| --- | --- |
| Mannitol | 4.2 kg |
| Purified water | 25.2 L |

(5) Preparation of Additive Granulated Powder

Ground mannitol (9.45 kg), low-substituted hydroxypropylcellulose (LH-33, 1.5 kg), crystalline cellulose (1.5 kg), crosspovidone (0.75 kg) and aspartame (0.45 kg) were placed into a fluidized bed granulation drier [manufactured by Powrex, FD-WSG-15 type], the material was fluidized at an air supplying temperature of 67° C. and an air supplying amount of 4 m³/min, a total amount of a solution in which mannitol (0.75 kg) and citric acid anhydride (0.15 kg) had been dissolved in purified water (5.1 kg) was sprayed at a feeding rate of 87 g/min and, after completion of spraying, drying was performed until an outlet air temperature became 45° C., to obtain a dried powder. The resulting dried powder was subjected to particle size adjustment with a power mill [manufactured by Showa kagakukikaikousakusho] having a screen size of 1.5 mm φ to obtain an additive granulated powder.

(6) Preparation of Mixed Powder

The aforementioned (4) overcoated enteric core-containing powder (5.294 kg), the aforementioned (5) additive granulated powder (5.926 kg) and a flavor (STRAWBERRY DURAROME, manufactured by Japan Filmenich (K.K.), 0.06 kg) were placed into a tumbler mixer [manufactured by Showa Kagakukikaikousakusho, TM-60S type], the materials were mixed for 5 minutes at a rotation speed of 20 min$^{-1}$, magnesium stearate (0.12 kg) was added, and the materials were further mixed for 1 minute at a rotation speed of 20 min$^{-1}$ to obtain a mixed powder.

(7) Preparation of Oral Disintegrating Tablet

The aforementioned mixed powder (1 kg) was compressed using a rotary compressing machine [manufactured by Kikusuiseisakusho, Correct 19K type] so that one tablet became 285 mg and a compressing pressure with a pestle having a 9 mm φ Flat beveled edge became about 19 kN/pestel. Upon this, two levels of a mixed powder at room temperature (21° C.) and a mixed powder warmed to 50° C. with a constant temperature machine were used, and two levels of the case where a compressing machine was at room temperature (21° C.) (normal case) and the case where a space in which a powder feeding part as well as a mortar and a pestle were disposed and which was surrounded by a safe cover (referred to as compressing chamber in Examples below) was warmed to 40° C. to 50° C. by warm air were used. Compression was performed rapidly so that a temperature of a warmed mixed powder was not lowered and, at the same time, warming of a compressing chamber with warm air was continued also during compression. In Examples below, the case where a mixed powder at room temperature is compressed with a compressing machine at room temperature is referred to as conventional conditions, and a method of compression by warming both of or either of a mixed powder and a compressing machine is referred to as compression under warming.

(8) Effect of Compression Under Warming

Hardness of the resulting tablet and the dissolution rate in an acidic solution (referred to as the dissolved percentage in the acid stage in Examples below; as the dissolved percentage in the acid stage is lower, the acid resistance is excellent) were as in Table 1.

TABLE 1

Comparison of dissolved percentages in acid stage between the presence and the absence of warming mixed powder and between the presence or the absence of warming in compressing

| | | Compressing machine | | | |
| --- | --- | --- | --- | --- | --- |
| | | Room temperature Dissolved percentage in acid stage | Warming | Room temperature Hardness | Warming |
| Mixed powder | Room temp. | 9.2% | 2.2% | 30N | 48N |
| | Warming | 6.6% | 0.8% | 32N | 42N |

As shown in Table 1, by warming both of the mixed powder and the compressing machine, the dissolved percentage in the acid stage was improved to 0.8%, that is, about ¹/₁₀ of 9.2% under conventional conditions, but when this warmed mixed powder was cooled again to room temperature, and compressed under conventional conditions, the dissolved percentage in the acid stage became 5.8%.

In other words, the dissolved percentage in the acid stage was improved from 9.2% to 5.8% by, as pre-treatment, once warming a mixed powder and compressing the powder under conventional conditions, and the acid resistance was further improved and the dissolved percentage in the acid stage became 0.8% by maintaining the warming state during compression.

In addition, even at the same level of a compressing pressure, hardness was risen by warming a compressing machine.

Example 2

The following (1) to (5) are the same as those in Example 1.
(1) Preparation of core-containing powder
(2) Preparation of undercoating film coated core-containing powder
(3) Preparation of enteric core-containing powder
(4) Preparation of enteric core-containing powder overcoated with mannitol
(5) Preparation of additive granulated powder
(6) Preparation of mixed powder
(7) Preparation of oral disintegrating tablet The aforementioned (6) mixed powder (1 kg) was compressed into two kinds of tablets having different sizes and weights (hereinafter, abbreviated as tablet A and tablet B) using a rotary compressing machine [manufactured by Kikusuiseisakusyo, Correct 19K type]. Tablet A was compressed so that one tablet became 285 mg and hardness with a pestle having a 9 mm φ Flat beveled edge became around 25 N, and tablet B was compressed so that one table became 570 mg and hardness with a pestle having a 12 mm φ Flat beveled edge became around 36 N.

Upon this, a mixed powder was warmed with a constant temperature machine, and rapidly compressed so that a temperature of mixed powder was not lowered and, at the same time, a compressing chamber in a compressing machine was warmed with warm air before compression and during compression, whereby, an average temperature of the mixed powder and the compressing machine became a warming level of room temperature to 40° C.

(8) Effect of Compression Under Warming

Regarding tablet A, hardness and the dissolved percentage in the acid stage of the resulting tablet were as in Table 2. The symbol * in Table 2 indicates the conventional conditions and the conditions under which both of the mixed powder and the compressing machine are warmed as shown in Example 1.

TABLE 2

Relationship between warming level as well as dissolved percentage in acid stage, hardness and compressing pressure: Tablet A

| | | Dissolved percentage in acid stage | Hardness | Compressing pressure |
|---|---|---|---|---|
| Warming level | 21° C.* | 9.2% | (30N) | (19 kN) |
| | 26° C. | 4.3% | 26N | 15 kN |
| | 32° C. | 2.9% | 25N | 13 kN |
| | 37° C. | 1.4% | 24N | 11 kN |
| | 46° C.* | 0.8% | (42N) | (19 kN) |

As shown in Table 2, as the warming level of the mixed powder and the compressing machine was a higher temperature, the dissolved percentage in the acid stage became lower. In addition, even at the same level of hardness, as the warming level was a higher temperature, the lower compressing pressure was obtained, that is, at the same level of a compressing pressure, hardness could be enhanced.

Regarding tablet B, hardness and the dissolved percentage in the acid stage of the resulting tablet are as shown in Table 3. The symbol * in Table 3 indicates the case where the mixed powder at room temperature was compressed with a compressing machine at room temperature.

TABLE 3

Relationship between warming level as well as dissolved percentage in acid stage, hardness and compressing pressure: Table B

| | | Dissolved percentage in acid stage | Hardness | Compressing pressure |
|---|---|---|---|---|
| Warming level | 23° C.* | 5.6% | 35N | 26 kN |
| | 28° C. | 4.2% | 36N | 25 kN |
| | 38° C. | 1.4% | 38N | 22 kN |

As shown in Table 3, as the warming level of the mixed powder and the compressing machine was higher temperature, the acid resistance level was lowered. In addition, even at the same level of hardness, as the warming level was a higher temperature, the lower compressing powder was obtained, that is, at the same level of a compressing pressure, hardness could be enhanced.

In addition, regarding tablet A and tablet B, when the warming levels were the same, the dissolved percentages in the acid stage were the same.

Example 3

(1) Preparation of Core-Containing Powder

Nonparel 105 (trade name, particle diameter: 100 to 200 μm, 41.58 kg) was placed in a tumbling fluidized-type coating granulator [manufactured by Powlech, MP-400 type], an inlet air temperature was controlled so that an outlet air temperature at the stationary state became about 31° C., and a pre-prepared bulk solution having the following composition was spray-coated at a feeding rate of 1.4 kg/min by a tangential spraying manner. A prescribed amount (257.6 kg) of the bulk solution was sprayed, and then, the following (2) Preparation of undercoating film coated core-containing powder was performed.

| [Bulk solution] | |
|---|---|
| Lansoprazole | 39.6 kg |
| Magnesium carbonate | 13.2 kg |
| Low-substituted hydroxypropylcellulose LH-32 (Hydroxypropoxyl group content: 8.8% by weight) | 6.6 kg |
| Hydroxypropylcellulose (type SL) | 13.2 kg |
| Purified water | 185 L |

(2) Preparation of Undercoating Film Coated Core-Containing Powder

Following the aforementioned (1) Preparation of core-containing powder, an inlet air temperature was controlled so that an outlet air temperature at the stationary state became about 41° C. and a pre-prepared undercoating film solution having the following composition was sprayed at a feeding rate of 1.2 kg/min by a tangential spraying manner. A prescribed amount (132.0 kg) of the film solution was sprayed and, at that time, spraying was stopped, drying was performed as it was for about 10 minutes, and the material was classified by a No. 42 round sieve (350 μm) and a No. 100 round sieve (150 μm) to obtain an undercoating film coated core-containing powder (132 kg).

| [Undercoating film solution] | |
|---|---|
| Hydroxypropylmethylcellulose (Type 2910, viscosity; 3 centistokes) | 9.24 kg |
| Titanium oxide (TiO$_2$) | 3.96 kg |
| Sterilized talc [manufactured by Matsumurasangyo (K. K.)] | 3.96 kg |
| Low-substituted hydroxypropylcellulose LH-32 (Hydroxypropoxyl group content: 8.8% by weight) | 6.6 kg |
| Mannitol | 9.24 kg |
| Purified water | 99.0 L |

(3) Preparation of Enteric Core-Containing Powder

The aforementioned (2) undercoating film coated core-containing powder (44.0 kg) was placed in a tumbling fluidized-type coating granulator [manufactured by Powlech, MP-400 type], an inlet air temperature was controlled so that an outlet air temperature at the stationary state became about 42° C., and a prescribed amount (54.6 kg) of a pre-prepared enteric film solution (A) having the following composition was sprayed at a feeding rate of 1.05 kg/min by a tangential spraying manner.

| [Enteric film solution (A)] | |
|---|---|
| Eudragit L30D-55 | 32.05 kg |
| Eudragit NE30D | 3.570 kg |
| Polyethylene glycol 6000 | 1.071 kg |
| Monostearic acid glycerin | 0.629 kg |
| Polysorbate 80 | 0.189 kg |
| Iron sesquioxide | 0.006 kg |
| Yellow Iron sesquioxide | 0.006 kg |
| Citric acid anhydride | 0.013 kg |
| Purified water | 44.3 L |

Subsequently, an inlet air temperature was controlled so that an outlet air temperature at the stationary state became about 42° C., and a prescribed amount (201.6 kg) of a pre-prepared enteric film solution (B) having the following composition was sprayed at a feeding rate of 1.00 kg/min by a tangential spraying manner.

| [Enteric film solution (B)] | |
|---|---|
| Eudragit L30D-55 | 117.6 kg |
| Eudragit NE30D | 13.06 kg |
| Triethyl citrate | 7.854 kg |
| Monostearic acid glycerin | 2.521 kg |
| Polysorbate 80 | 0.756 kg |
| Iron sesquioxide | 0.025 kg |
| Yellow iron sesquioxide | 0.025 kg |
| Citric acid anhydride | 0.021 kg |
| Purified water | 59.7 L |

Subsequently, an inlet air temperature was controlled so that an outlet air temperature at the stationary state became about 42° C., and a prescribed amount (27.3 kg) of a pre-prepared enteric film solution (A) having the following composition was sprayed at a feeding rate of 1.05 kg/min by a tangential spraying manner.

(4) Preparation of Enteric Core-Containing Powder Overcoated with Mannitol

Following the above (3), an inlet air temperature was controlled so that an outlet air temperature at the stationary state became about 42° C., and a pre-prepared film solution having the following composition was sprayed at a feeding rate of 0.90 kg/min by a tangential spraying manner. A prescribed amount (29.4 kg) thereof was sprayed and, at that time, spraying was stopped, drying was continued as it was until an outlet air temperature reached 65° C., and the material was cooled. This was classified using a No. 35 round sieve (420 μm) and a No. 60 round sieve (250 μm) to obtain an overcoated enteric core-containing powder (106 kg).

An average particle diameter of the resulting overcoated enteric core-containing powder was 357 μm.

| [Film solution] | |
|---|---|
| Mannitol | 4.2 kg |
| Purified water | 25.2 L |

(5) Preparation of Additive Granulated Powder

Ground mannitol (75.6 kg), low-substituted hydroxypropylcellulose (LH-33, 12 kg), crystalline cellulose (12 kg), crosspovidone (6 kg) and aspartame (3.6 kg) were placed into a fluidized bed granulation drier [manufactured by Glatt, WSG120], the mixture was fluidized at a air supplying temperature of 90° C. and an air supplying amount of 1700 m$^3$/hr, and a solution in which mannitol (7.38 kg) and citric acid anhydride (1.476 kg) had been dissolved in purified water (50.2 L) was sprayed. A rate of feeding the solution was initiated at 1200 g/min, the rate was regulated from 750 g/min to 650 g/min during feeding, and a prescribed amount (48 kg) of the solution was sprayed and, at that time, spraying was stopped. After completion of spraying, an air supplying amount was regulated from 1700 m$^3$/hr to 1600 m$^3$/hr, and drying was performed until an outlet air temperature became 58° C., to obtain a dried powder. The resulting dried powder was subjected to particle size adjustment with Comil having a screen size of 1.5 mm φ [manufactured by Quadro], to obtain an additive granulated powder.

(6) Preparation of Mixed Powder

The aforementioned (4) overcoated enteric core-containing powder (108.88 kg), the aforementioned (5) additive granulated powder (115.55 kg) and a flavor (STRAWBERRY DURAROME, Japan Filmenich (K.K.), 1.2 kg) were placed in a V-type mixer [manufactured by Pharmatech, 800L], mixing was performed for 10 minutes at a rotation speed of 10 min$^{-1}$, magnesium stearate (2.4 kg) was further added, and mixing was performed for 1 minute at a rotation speed of 5 min$^{-1}$ to obtain a mixed powder.

(7) Preparation of Oral Disintegrating Tablet

The (6) mixed powder (7.4 kg) was compressed using a rotary compressing machine [manufactured by Fette, 2090 type] so that one tablet became 285 mg and a compressing pressure with a pestle having a 9 mm φ Flat beveled edge became about 17 kM/pestle. Two levels of a compressing machine rotation speed of 39 min$^{-1}$ (100 thousands tablets/hr) and 50 min$^{-1}$ (129 thousands tablets/hr) were used.

Upon this, the mixed powder was warmed with a constant temperature machine, and a compressing chamber, mainly a rotary turn table was warmed with warm air before compression in a compressing machine, so that an average temperature of the mixed powder and the compressing machine. became a warming level of room temperature (20° C.) to 40° C.

(8) Effect of Compression Under Warming

The dissolved percentages in the acid stage of tablets obtained at respective compressing machine rotation speeds are as in Table 4 and Table 5.

TABLE 4

Dissolved percentage in acid stage upon compression under warming at compressing machine rotation speed 39 min$^{-1}$

| Mixed powder warming level | | Compressing machine warming level | | | |
|---|---|---|---|---|---|
| | | Room temperature (20° C.) | 25° C. | 30° C. | 40° C. |
| Room temperature | (20° C.) | 8.1% | | 4.6% | 3.4% |
| | 30° C. | | 5.9% | 4.4% | 3.6% |
| | 40° C. | | 1.9% | 2.9% | 1.4% |

TABLE 5

Dissolved percentage in acid stage upon compression under warming at compressing machine rotation speed 50 min$^{-1}$

| Mixed powder warming level | | Compressing machine warming level | | | |
|---|---|---|---|---|---|
| | | Room temperature (20° C.) | 25° C. | 30° C. | 40° C. |
| Room temperature | (20° C.) | 7.8% | | 4.6% | 3.5% |
| | 30° C. | | 5.7% | 3.9% | 3.8% |
| | 40° C. | | 1.9% | 2.9% | 1.4% |

As shown in Table 4 and Table 5, as a warming level for the mixed powder and the compressing machine were a higher temperature, the dissolved percentage in the acid stage was lowered.

In addition, it had been found heretofore that when a compressing machine rotation speed is decreased and a compressing rate during compression is decreased, the acid resistance can be improved under conventional conditions (a temperature mixed powder and that of compressing machine are both room temperature) and, for example, in order to improve the dissolved percentage in the acid stage to 3 to 5%, it was necessary to decrease a compressing machine rotation speed to around 10 min$^{-1}$. By compression under warming, the dissolved percentage in the acid stage could be improved without decreasing a compressing machine rotation speed.

In addition, harnesses of tablets obtained at respective compressing machine rotation speeds are as in Table 6 and Table 7.

TABLE 6

Tablet hardness upon compression under warming at compressing machine rotation speed 39 min$^{-1}$

| Mixed powder warming level | | Compressing machine warming level | | |
|---|---|---|---|---|
| | | Room temperature (20° C.) | 30° C. | 40° C. |
| Room temperature | (20° C.) | 22N | 27N | 31N |
| | 30° C. | | 27N | 28N |
| | 40° C. | | 27N | 27N |

TABLE 7

Tablet hardness upon compressing under warming at compressing machine rotation speed 50 min$^{-1}$

| Mixed powder warming level | | Compressing machine warming level | | |
|---|---|---|---|---|
| | | Room temperature (20° C.) | 30° C. | 40° C. |
| Room temperature | (20° C.) | 24N | 26N | 29N |
| | 30° C. | | 27N | 27N |
| | 40° C. | | 26N | 28N |

As shown in Table 6 and Table 7, the tablet hardness was enhanced by compression under warming as compared with that under conventional conditions.

Example 4

A turn table (diameter 520 mm φ) of a rotary compressing machine for industrial production (manufactured by Kikusuisha, number of pestles; 45) was warmed with a contact-type resistance heater attached to the turn table, and it was confirmed that a temperature of the turn table was risen to the desired temperature. As the contact-type resistance heater, a sheet-like silicone rubber heater (262.5 W/450 cm$^2$) was used and, by adjusting a voltage, a heater temperature was set to be 45, 50, 55 or 60° C., followed by studying.

The result are shown in Table 8. It was confirmed that the turn table of the rotary compressing machine was warmed to the desired temperature (30 to 40° C.) with the contact-type resistance heater.

TABLE 8

Relationship between warming temperature and warming time of turn table

| Warming time | Contact-type heater temperature | | | |
|---|---|---|---|---|
| | 45° C. | 50° C. | 55° C. | 60° C. |
| 0 hrs | 20.5 | 21.6 | 22.3 | 19.6 |
| 1 hrs | 28.9 | — | 33.0 | 33.1 |
| 2 hrs | 30.8 | 33.1 | 35.5 | 36.3 |
| 3 hrs | — | — | 36.9 | 38.4 |
| 4 hrs | 33.1 | 36.5 | 38.4 | 39.9 |
| 6 hrs | 34.5 | 37.4 | 40.3 | 42.0 |
| 8 hrs | 35.0 | 38.8 | 41.0 | 43.1 |

Example 5

(1) Pre-Heating Warming of Compressing Machine

A turn table (diameter 535 mm φ), an upper pestle holder and a lower pestle holder of a rotary compressing machine for industrial production (manufactured by Fette, 2090 type) were warmed with a contact-type resistance heater, and a temperature of the turn table was risen to 45° C. As the contact-type resistance heater, a sheet-like silicone rubber heater (total: 975 W) was used.

(2) Preparation of Oral Disintegrating Tablet

A mixed powder (room temperature, 55 kg) prepared by the same manner as that of the item (6) in Example 3 was compressed with the rotary compressing machine (manufactured by Fette, 2090 type) pre-heated in (1), so that one tablet became 570 mg, and hardness with a pestle having a 12 mm φ Flat beveled edge became 37 N. A compressing machine rotation speed was 39 min$^{-1}$ (100 thousands tablets/hr) or 50 mm$^{-1}$ (125 thousands tablets/hr), and sampling was performed when a temperature of the turn table was 28 to 36° C.

As a control, a tablet was prepared at a temperature of a turn table of room temperature (mixed powder was also room temperature), and the dissolved percentage in the acid stage was compared with the tablet obtained by pre-heating the turn table.

(3) Effect of Compression Under Warming

The dissolved percentages in the acid stage of tablets obtained at respective compressing machine rotation speed are summarized in Table 9. As a result, it was shown that, when compression was performed by warming the rotary compressing machine for industrial production with the contact-type resistance heater, the dissolved percentage in the acid stage was lowered, and the acid resistance was more improved as compared with compression at room temperature.

Table 9
Relationship Between Turn Table Temperature and Dissolved Percentage in Acid Stage

| | Compressing machine rotation speed | | |
|---|---|---|---|
| | 15 min$^{-1}$ | 39 min$^{-1}$ | 50 min$^{-1}$ |
| Room temperature (20° C.) | 5.9% | 7.9% | 8.2% |
| 28 ± 1° C. | — | 6.0% | 5.7% |
| 35 ± 1° C. | — | 4.6% | 4.3% |

INDUSTRIAL APPLICABILITY

As apparent from the foregoing, in the tablet obtainable by the method of the present invention, rupture of a coating film of coated granules is decreased. Therefore, in case of the tablet comprising enteric-coated granules containing a physiologically active substance which is unstable to an acid, dissolution in the presence an acid such as in stomach is improved. In addition, hardness of the tablet is improved.

The invention claimed is:
1. A method of manufacturing a tablet, which comprises the steps of:
   warming a mixture of enteric-coated granules containing a physiologically active substance and additive(s) to 25° C. or higher; and
   compressing the mixture at a predetermined temperature of 25° C. or higher, wherein the physiologically active substance is a physiologically active substance which is unstable to an acid, and wherein the manufacturing process includes a temperature controlling tool for maintaining the temperature of the mixture of enteric-coated granules and additive(s) upon compressing at the predetermined temperature.

2. The method according to claim 1, wherein the physiologically active substance which is unstable to an acid is a proton pump inhibitor (PPI).

3. The method according to claim 2, wherein the PPI is a benzimidazole compound or a salt thereof.

4. The method according to claim 3, wherein the benzimidazole compound is lansoprazole or an optically active isomer thereof.

5. The method according to claim 1, wherein the enteric coating layer contains an aqueous enteric polymer base.

6. The method according to claim 5, wherein the aqueous enteric polymer base is a methacrylic copolymer.

7. The method according to claim 1, wherein the enteric-coated granules are warmed to a temperature of 25° C. to 50° C., followed by compressing at a temperature of 25° C. to 50° C.

8. The method according to claim 1, wherein the enteric-coated granules are warmed to a temperature of 25° C. to 40° C., followed by compressing at a temperature of 25° C. to 40° C.

9. The method according to claim 1, wherein the tablet is an oral disintegrating tablet.

10. The method according to claim 1, wherein a tablet compressing machine is warmed to warm the granules to 25° C. or higher for compressing the granules at 5° C. or higher.

11. The method according to claim 10, wherein the tablet compressing machine is a rotary tablet compressing machine, and compressing is performed after a rotary turn table thereof is warmed.

12. A method of decreasing rupture of a coating film of enteric-coated granules containing a physiologically active substance, which comprises warming a mixture of the enteric-coated granules and additive(s) to 25° C. or higher, followed by compressing the mixture at a predetermined temperature of 25° C. or higher, wherein the physiologically active substance is a physiologically active substance which is unstable to an acid, and wherein the method includes the use of a temperature controlling tool for maintaining the temperature of the mixture of enteric-coated granules and additive(s) upon compressing at the predetermined temperature.

13. A method of reducing the dissolved percentage in the acid stage of a tablet comprising warming a mixture of the enteric-coated granules and additive(s) to 25° C. or higher, followed by compressing the mixture at a predetermined temperature of 25° C. or higher, wherein the tablet comprises enteric-coated granules containing a physiologically active substance and the physiologically active substance is a physiologically active substance which is unstable to an acid, and wherein the method includes the use of a temperature controlling tool for maintaining the temperature of the mixture of enteric-coated granules and additive(s) upon compressing at the predetermined temperature.

14. A method of improving hardness of a tablet, which comprises warming a mixture of the enteric-granules containing a physiologically active substance and additive(s) to 25° C. or higher, followed by compressing the mixture at a predetermined temperature of 25° C. or higher, wherein the physiologically active substance is a physiologically active substance which is unstable to an acid, and wherein the method includes the use of a temperature controlling tool for maintaining the temperature of the mixture of enteric-coated granules and additive(s) upon compressing at the predetermined temperature.

15. A tablet obtainable by the manufacturing process of claim 1 that includes coating a composition containing a physiologically active substance with an enteric coating layer, adding additive(s) to the resulting enteric-coated granules, warming a mixture of the enteric-coated granules and the additive(s) to 25° C. or higher, followed by compressing the mixture at 25° C. or higher, wherein the physiologically active substance is a physiologically active substance which is unstable to an acid.

16. The tablet according to claim 15, wherein the physiologically active substance which is unstable to an acid is PPI of a benzimidazole compound or a salt thereof.

17. The tablet according to claim 16, wherein the benzimidazole compound is lansoprazole or an optically active isomer thereof.

18. A tablet obtainable by the method of claim 13, comprising a physiologically active substance which is unstable to an acid, wherein the tablet has a dissolved percentage in the acid stage that is improved by tablet compression under warming at 25° C. or higher.

19. A tablet obtainable by the method of claim 14, comprising a physiologically active substance which is unstable to an acid, wherein the tablet has a hardness that is increased by tablet compression under warming at 25° C. or higher.

20. A tablet obtainable by the method of claim 12 comprising enteric-coated granules comprising a physiologically active substance which is unstable to an acid, and wherein rupture of a coating film of the enteric-coated granules is decreased by tablet compression under warming at 25° C. or higher.

21. The method according to claim 1, wherein an ambient temperature of a compressing chamber for compressing the enteric-coated granules is monitored.

22. The method according to claim 10, wherein the tablet compressing machine is warmed to warm the granules to 25° to 50° C., and the temperature for compressing the granules is 25° C. to 50° C.

23. The method according to claim 10, wherein the tablet compressing machine is warmed to warm the granules to 25° to 40° C., and the temperature for compressing the granules is 25° C. to 40° C.

24. The method of claim 12, wherein the enteric-coated granules are warmed to 25° C. to 50° C., followed by compressing the granules at 25° C. to 50° C.

25. The method of claim 12, wherein the enteric-coated granules are warmed to 25° C. to 40° C., followed by compressing the granules at 25° C. to 40° C.

26. The method of claim 13, wherein the enteric-coated granules are warmed to 25° C. to 50° C., followed by compressing the granules at 25° C. to 50° C.

27. The method of claim 13, wherein the enteric-coated granules are warmed to 25° C. to 40° C., followed by compressing the granules at 25° C. to 40° C.

28. The method of claim 14, wherein the enteric-coated granules are warmed to 25° C. to 50° C., followed by compressing the granules at 25° C. to 50° C.

29. The method of claim 14, wherein the enteric-coated granules are warmed to 25° C. to 40° C., followed by compressing the granules at 25° C. to 40° C.

30. The method of claim 15, wherein the mixture is warmed to 25° C. to 50° C., followed by compressing the mixture at 25° C. to 50° C.

31. The method of claim 15, wherein the mixture is warmed to 25° C. to 40° C., followed by compressing the mixture at 25° C. to 40° C.

32. The tablet of claim 18, wherein the tablet compression under warming is at 25° C. to 50° C.

33. The tablet of claim 18, wherein the tablet compression under warming is at 25° C. to 40° C.

34. The tablet of claim 19, wherein the tablet compression under warming is at 25° C. to 50° C.

35. The tablet of claim 19, wherein the tablet compression under warming is at 25° C. to 40° C.

36. The tablet of claim 20, wherein the tablet compression under warming is at 25° C. to 50° C.

37. The tablet of claim 20, wherein the tablet compression under warming is at 25° C. to 40° C.

\* \* \* \* \*

UNITED STATES PATENT AND TRADEMARK OFFICE
CERTIFICATE OF CORRECTION

PATENT NO. : 8,765,176 B2
APPLICATION NO. : 10/477478
DATED : July 1, 2014
INVENTOR(S) : Yamamoto et al.

It is certified that error appears in the above-identified patent and that said Letters Patent is hereby corrected as shown below:

Title page, (73) "Assignee": "Takeda Pharmaceutical Campany Limited, Osaka (JP)" should be
-- Takeda Pharmaceutical Company Limited, Osaka (JP) --.

Signed and Sealed this
Seventh Day of April, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,765,176 B2 | Page 1 of 1 |
| APPLICATION NO. | : 10/477478 | |
| DATED | : July 1, 2014 | |
| INVENTOR(S) | : Keiichi Yamamoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this
Eighth Day of March, 2016

Michelle K. Lee
*Director of the United States Patent and Trademark Office*